(12) United States Patent
Durkin et al.

(10) Patent No.: US 7,304,724 B2
(45) Date of Patent: Dec. 4, 2007

(54) METHOD AND APPARATUS FOR QUANTIFICATION OF OPTICAL PROPERTIES OF SUPERFICIAL VOLUMES

(75) Inventors: Anthony J. Durkin, Irvine, CA (US); Sheng-Hao Tseng, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 297 days.

(21) Appl. No.: 11/104,033

(22) Filed: Apr. 12, 2005

(65) Prior Publication Data

US 2005/0226548 A1  Oct. 13, 2005

Related U.S. Application Data

(60) Provisional application No. 60/561,836, filed on Apr. 13, 2004.

(51) Int. Cl.
*G01N 21/00* (2006.01)
(52) U.S. Cl. .................. 356/73; 356/326; 356/446; 600/310
(58) Field of Classification Search ................ 356/326, 356/446, 73; 600/310
See application file for complete search history.

(56) References Cited

U.S. PATENT DOCUMENTS

| 5,424,843 | A | | 6/1995 | Tromberg et al. |
| 5,640,247 | A | * | 6/1997 | Tsuchiya et al. ............ 356/446 |
| 6,377,841 | B1 | * | 4/2002 | Lin et al. ..................... 600/477 |
| 6,535,278 | B1 | * | 3/2003 | Imura ........................... 356/73 |
| 6,571,118 | B1 | * | 5/2003 | Utzinger et al. ............. 600/476 |
| 6,678,541 | B1 | | 1/2004 | Durkin et al. |
| 7,139,076 | B1 | * | 11/2006 | Marbach ...................... 356/446 |
| 2002/0071118 | A1 | * | 6/2002 | Shinbori et al. ............. 356/326 |
| 2003/0023172 | A1 | | 1/2003 | Tromberg et al. |

OTHER PUBLICATIONS

Bevilacqua et al., In vivo local determination of tissue optical properties: applications to human brain, App. Optics, vol. 38, No. 22, Aug. 1999.
Amelink et al., In vivo measurement of the local optical properties of tissue by use of differential path-length spectroscopy, Optics Letters, vol. 29, No. 10, May 15, 2004.

* cited by examiner

*Primary Examiner*—Gregory J. Toatley, Jr.
*Assistant Examiner*—Kara Geisel
(74) *Attorney, Agent, or Firm*—Vista IP Law Group LLP

(57) ABSTRACT

A device and method for accurately performing quantitative diffuse optical spectroscopy on a sample includes a light source and a source optical fiber that is optically coupled to the light source. A diffuser material is interposed between the source optical fiber and the sample, the diffuser material comprising a high scattering, low absorption material. The diffuser material effectively increases the photon path length from the light source to the sample, which limits the depth of interrogation to superficial volumes despite the penetrating nature of the radiation typically used. A detector optical fiber is provided adjacent to or laterally disposed from the source optical fiber. The detector optical fiber is coupled to a detector which detects photons collected in the detector optical fiber. The detector optical fiber and the source optical fiber may be separated by a distance of less than 5 mm while still permitting the diffusion approximation to remain valid.

19 Claims, 12 Drawing Sheets

METHOD AND APPARATUS FOR QUANTIFICATION OF OPTICAL PROPERTIES OF SUPERFICIAL VOLUMES

REFERENCE TO RELATED APPLICATIONS

This Application claims priority to U.S. Provisional Patent Application No. 60/561,836 filed on Apr. 13, 2004. The '836 application is incorporated by reference as if set forth fully herein.

STATEMENT REGARDING FEDERALLY SPONSORED RESEARCH AND DEVELOPMENT

The U.S. Government may have a paid-up license in this invention and the right in limited circumstances to require the patent owner to license others on reasonable terms as provided for by the terms of Grant No. RR01192 awarded by the National Institutes of Health (Laser Microbeam and Medical Program: LAMMP).

FIELD OF THE INVENTION

The field of the invention generally relates to methods and devices used in diffuse optical spectroscopy (DOS). More specifically, the field of the invention generally relates to diffuse optical spectroscopy methods and devices which are able to quantify optical properties in the superficial volumes of biological and non-biological materials.

BACKGROUND OF THE INVENTION

Diffuse optical spectroscopy (DOS) using frequency modulated light has been employed to quantify in-vivo tissue constituents as well as the optical properties of in-vivo tissue. Diffuse optical spectroscopy may also be used to quantify chromophore concentration in biological material. Diffusion approximation to the equation of radiative transport provides a useful modeling framework for diffuse optical spectroscopy methods, and generally gives an accurate description of light propagation in thick tissues provided detected photons have undergone at least 10 scattering events before they reach the detector. For example, U.S. Pat. No. 5,424,843 and U.S. patent application Publication No. 20030023172, both of which are incorporated by reference as if set forth fully herein, describe frequency domain spectroscopy methods and devices used in analyzing light scattered from a sample. While the '843 patent and the '172 published application provide a general framework for recovering chromophore concentration and optical properties, neither describes a means for accurately recovering these quantities for superficial tissues or under conditions when the source-detector separation becomes smaller than that allowed by diffusion approximation.

Consequently, current diffuse optical spectroscopy methods are limited to situations in which the reduced scattering coefficient, $\mu_s'$ is greater (by an order of magnitude) than the absorption coefficient, $\mu_a$. In practical terms, this limits the DOS technique to source-detector separations of about 5 mm in most tissues (with interrogation depths of about 2.5 mm), wavelengths between 650-1000 nm, and modulation frequencies between 50 and 600 MHz.

As source-detector separation is reduced to distances smaller than 5 mm, the validity of diffusion approximation is reduced along with ability to accurately recover optical properties and chromophore concentrations in existing diffuse optical spectroscopy methods and devices. As the distance between the source and detector becomes smaller, the average number of scattering events that photons experience before detection is also reduced. Similarly as one moves to more highly absorbing spectral domains (e.g., wavelengths shorter than 650 nm and wavelengths longer than 1000 nm), a reduction in source-detector separation is necessary in order to collect light with a reasonable signal to noise (SNR) ratio. In each of these scenarios, however, a simple application of diffusion approximation-based modeling will yield inaccurate tissue optical properties and chromophore concentrations.

U.S. Pat. No. 6,678,541, which is incorporated by reference as if set forth fully herein, discloses an optical fiber probe and methods for measuring optical properties. This approach, however, requires a multi-fiber probe geometry in order to recover tissue optical properties under continuous illumination. The disadvantage of a multi-fiber probe geometry is that each fiber samples a slightly different volume of tissue so there is inherent inaccuracy in the method.

With respect to the problem of quantifying superficial chromophores and their optical properties, prior methods have solved this by primarily using multivariate calibration techniques such as the method of Partial Least Squares (PLS). In this method, signals are acquired from a set of samples that are representative of the sample of interest. The concentration of the analyte of interest must be known for each sample included in the calibration. By sampling many "reference" samples, an empirical model relating spectral shapes to analyte concentration can be developed. The problem with this approach is that the calibration samples have to be very similar to the target (unknown) sample set of interest. In addition, there has to be a way of recovering the true concentration of the analyte of interest in each of those samples, using a separate method, so that a correlative model can be developed.

There thus is a need for device and method which can perform reliable diffuse optical spectroscopy measurements where the source-detector distance is reduced (for example, less than 5 mm). Reducing the distance between the source and detector while still allowing for accurate quantification using diffusion approximation would advantageously allow smaller probe-type devices to be manufactured. In addition, smaller source-detector distances would permit diffuse optical spectroscopy analysis of superficial volumes in biological tissue. The analysis of superficial volumes using diffuse optical spectroscopy has applications for the quantitative characterization of epithelial malignant transformation in tissues which generally occurs at depths of a few tens of microns to a few hundred microns. The method and device would also be able to determine the optical properties and even quantify chromophore (e.g., glucose) concentrations of tissue components in-vivo at superficial depths (tissue depths for determining interstitial tissue glucose concentration/distribution range from a few tens of microns to a few hundreds of microns depending on body site probed). The method and device would have potential intravascular applications to characterize vulnerable plaques, sub-surface pools of lipids, and inflammatory changes occurring in vascular tissue. The method and device would have potential applications in the assessment of effectiveness of pharmaceutical and/or cosmetic formulations that may be used to alter the appearance or "quality" of skin. For example, the device is particularly amenable to measuring changes in superficial tissue hydration. The method and device would have potential applications in the in-situ characterization of skin surface preparations such as sunscreens. Finally, the method may be used in connection with non-biological samples such as, for example, quantifying chemical species in tablet formulations.

SUMMARY OF THE INVENTION

The present invention is directed to a method and device used to quantify the optical properties of biological or even non-biological material. The method and device described herein reduces the source-detector separation distance while at the same time maintains the validity of existing diffusion approximation techniques. The method and device uses a diffuser which is made of a high scattering, low absorption material. The diffuser is interposed between the surface of the sample and the distal end of the optical fiber coupled to the radiation source. The high scattering, low absorption material effectively increases the photon path length and allows the source-detector separation to be made arbitrarily small.

In one aspect of the invention, the device includes at least one source optical fiber and at least one detector optical fiber. The diffuser is interposed between the surface of the sample to be imaged and the source of radiation within the source optical fiber arm of the device. The source and detector optical fibers may be laterally spaced from one another or located adjacent to one another. According to certain preferred embodiments of the invention, the source and detector optical fibers may be incorporated into a flexible elongate member (or in some cases an inflexible member) such as probe, catheter, guide wire or the like. With respect to a probe, the method and device may be used in endoscopic applications. The device may also be incorporated into a hollow core needle or trocar-type device which can then be used for biopsies (e.g., breast cancer biopsy). The device may also be delivered to the prostate gland or bladder in a transurethral manner.

In one aspect of the invention, a diffuse optical spectroscopy device for obtaining the optical properties of a sample includes a first light source, a first source optical fiber coupled to the first light source, a first detector optical fiber, the first detector optical fiber coupled to a detector, a second broadband light source, a second source optical fiber coupled to the second broadband light source, a second detector optical fiber, the second detector optical fiber coupled to a spectrometer, and a diffuser interposed between a distal end of the first source optical fiber and the sample, the diffuser comprising a material having a reduced scattering coefficient greater than 9 $mm^{-1}$.

In another aspect of the invention, a diffuse optical spectroscopy device for obtaining the optical properties of a sample includes a first light source, a first source optical fiber having a proximal end and a distal end, the first source optical fiber being optically coupled to the first light source at the proximal end, a first detector optical fiber having a proximal end and a distal end, the first detector optical fiber being optically coupled to a detector at the proximal end. The device further includes a broadband light source, a second source optical fiber having a proximal end and a distal end, the second source optical fiber being optically coupled to the broadband light source at the proximal end. The device further includes a spectrometer and a second detector optical fiber having a proximal end and a distal end, the second detector optical fiber being optically coupled to the spectrometer at the proximal end. A diffuser is interposed between the distal end of the first source optical fiber and the sample. The distal end of the first source optical fiber and the distal end of the first detector optical fiber are separated by a distance of less than 5 mm. The distal ends of the first source optical fiber and first detector optical fiber may be separated by a distance of around 2.5 mm while still maintaining the validity of the diffusion approximation.

In another aspect of the invention, a method of performing diffuse optical spectroscopy on a sample is described. The method employs a DOS device of the type described herein. The sample is illuminated with light from the first light source using a first source optical fiber, the light passing through the diffuser prior to reaching the sample. The reflected light is then detected with the detector coupled to a first detector optical fiber. The sample is then illuminated with light from the second light source (e.g., a broadband light source) using a second source optical fiber. The reflected light is then detected with the spectrometer coupled to a second detector optical fiber. The optical properties ($\mu_a$, $\mu_s'$) of the sample may then be obtained.

The device and method may even have applications for quality control and process monitoring in the pharmaceutical industry because drug formulations (e.g., tablets) are typically highly scattering yet the dimensions are not usually conducive to the usual photon migration-based quantitative analysis.

Asterisks represent 5 mm semi-infinite geometry measurements. Dash line is a fit to squares.

Figure 9A:
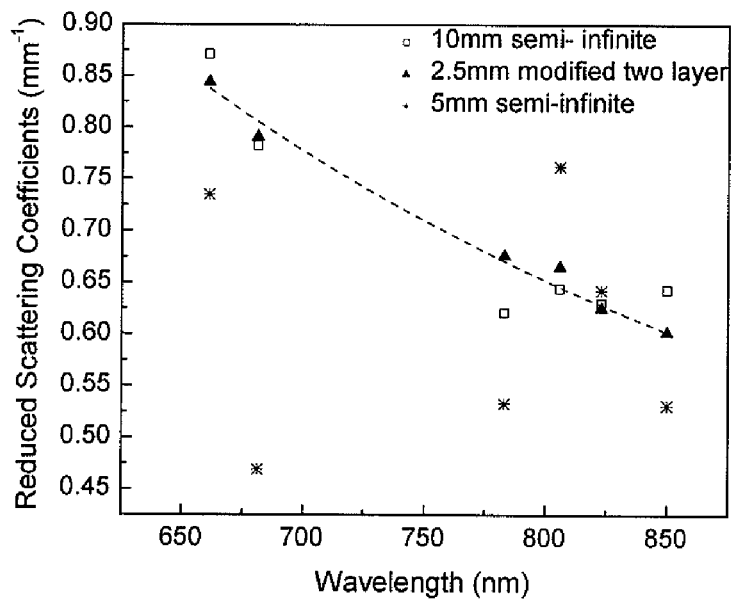
FIG. 9A illustrates the recovered optical properties of reduced scattering coefficients. Squares represent 10 mm semi-infinite geometry measurements. Solid triangles represent 2.5 mm modified two-layer geometry measurements.
Figure 9B:
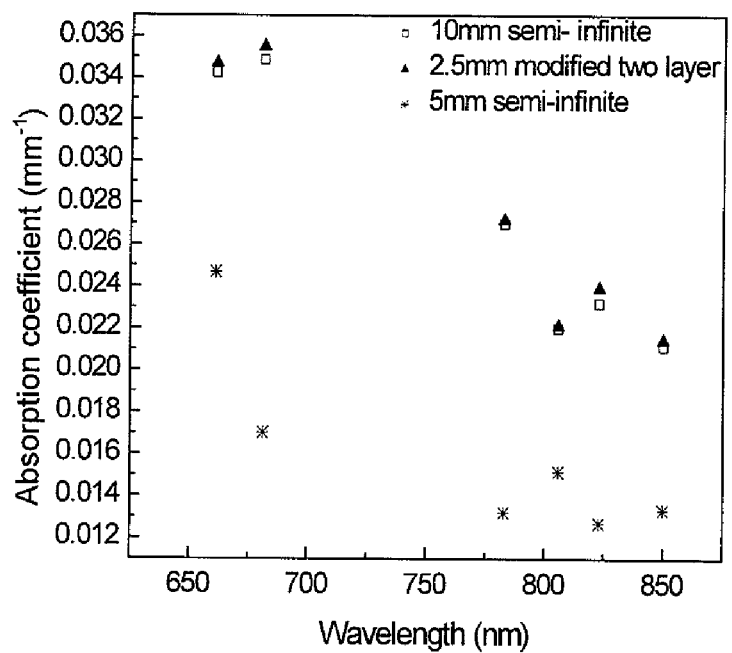

FIG. 9B illustrates the recovered optical properties of reduced absorption coefficients. Squares represent 10 mm semi-infinite geometry measurements. Solid triangles represent 2.5 mm modified two-layer geometry measurements. Asterisks represent 5 mm semi-infinite geometry measurements.

Figure 10A:
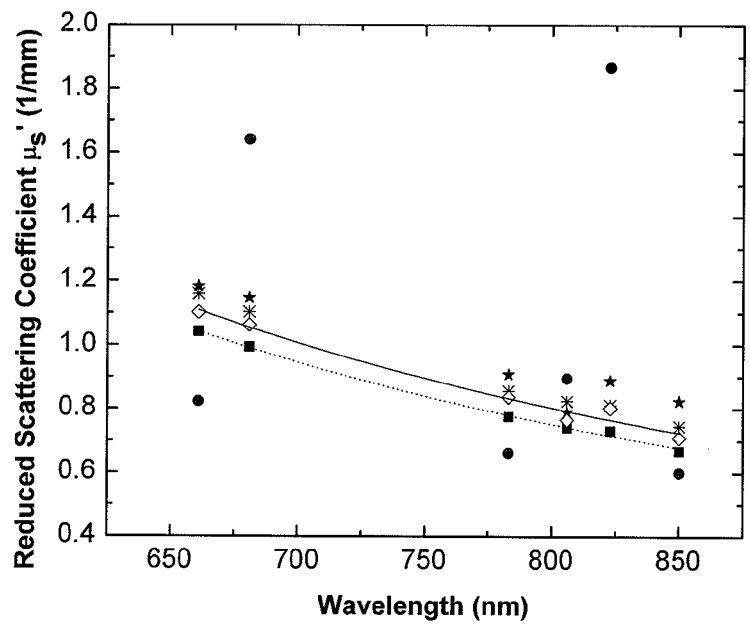

FIG. 10A illustrates the recovered measurement of $\mu_s'$ at six wavelengths for a sample having a low absorption and moderate scattering liquid phantom having optical properties similar to gingival (gum) tissue.

Figure 10B:
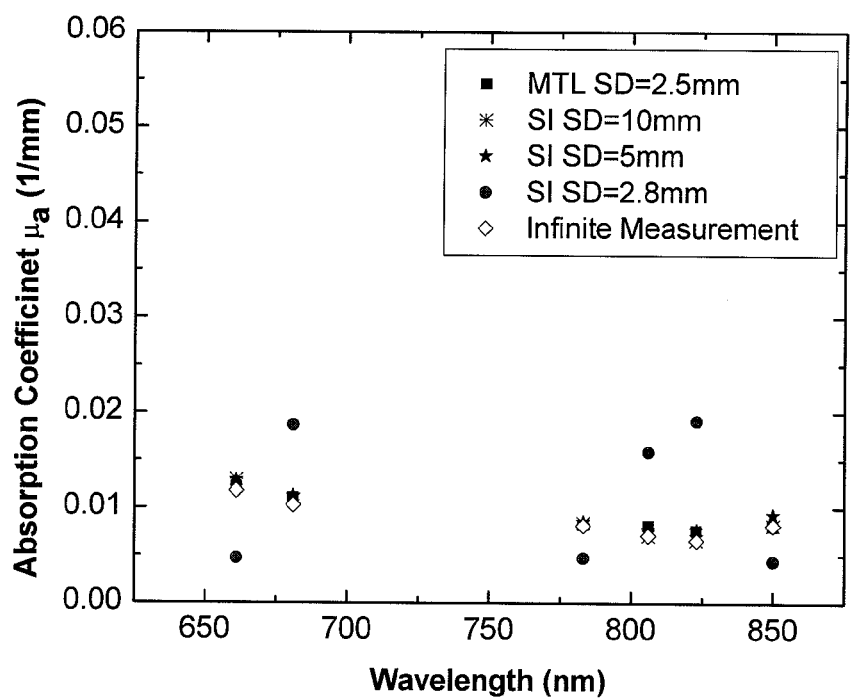

FIG. 10B illustrates the recovered measurement of $\mu_a$ at six wavelengths for a sample having a low absorption and moderate scattering liquid phantom having optical properties similar to gingival (gum) tissue.

Figure 11A:
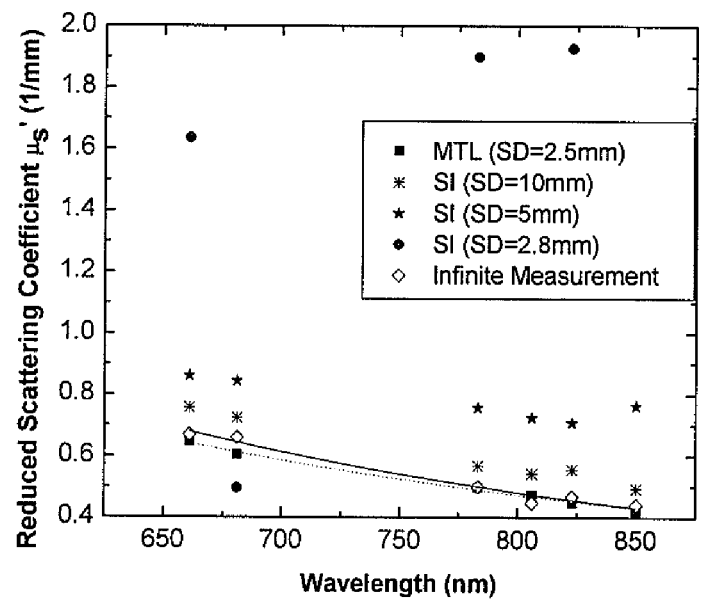

FIG. 11A illustrates the recovered measurement of $\mu_s'$ at six wavelengths for a sample having a low absorption and low scattering liquid phantom having optical properties similar to cheek tissue.

Figure 11B:
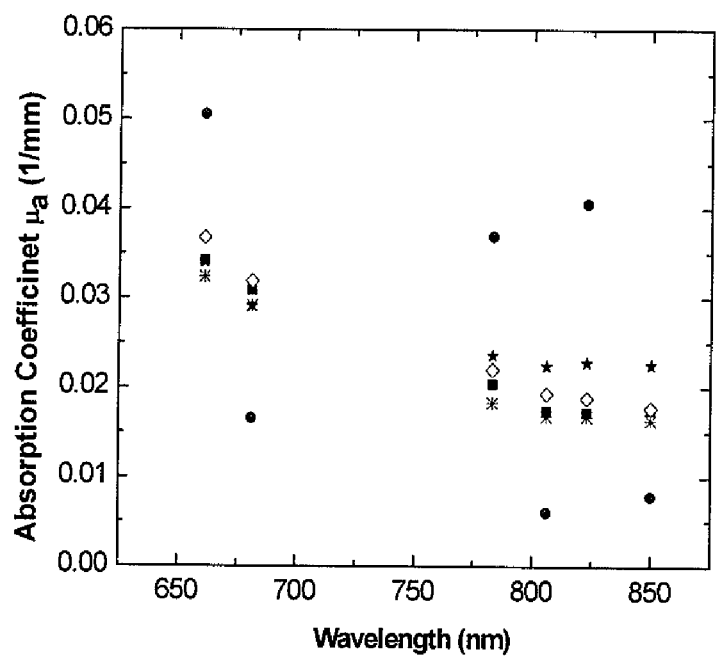

FIG. 11B illustrates the recovered measurement of $\mu_a$ at six wavelengths for a sample having a low absorption and low scattering liquid phantom having optical properties similar to cheek tissue.

Figure 12:
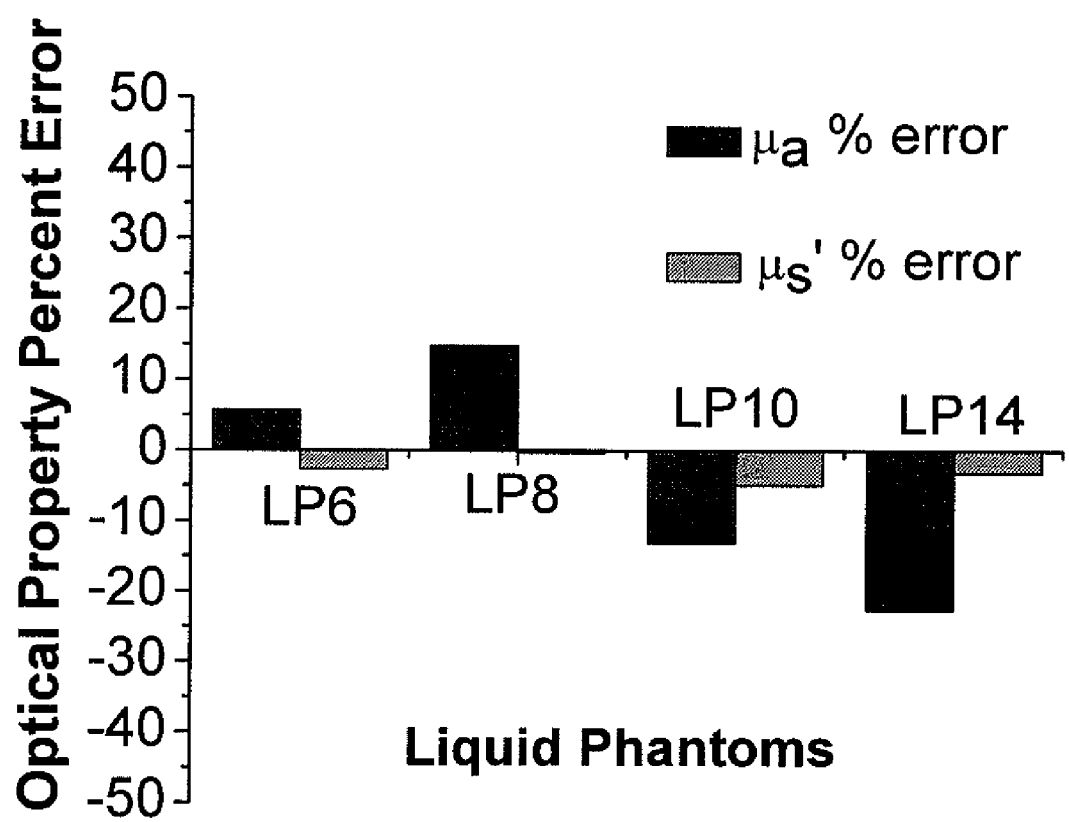

FIG. 12 is a graph illustrating the deviation of the derived optical properties from the true optical properties for each of the four liquid phantoms that were fabricated (LP6, LP8, LP10, LP14).

Figure 13A:
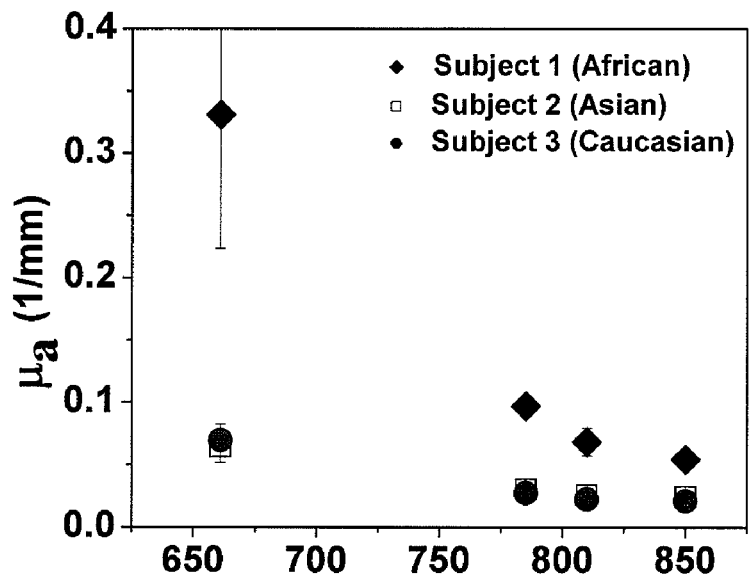

FIG. 13A illustrates the measured optical property ($\mu_a$) as a function of wavelength for three subjects of different racial ethnicities (African, Asian, Caucasian).

Figure 13B:
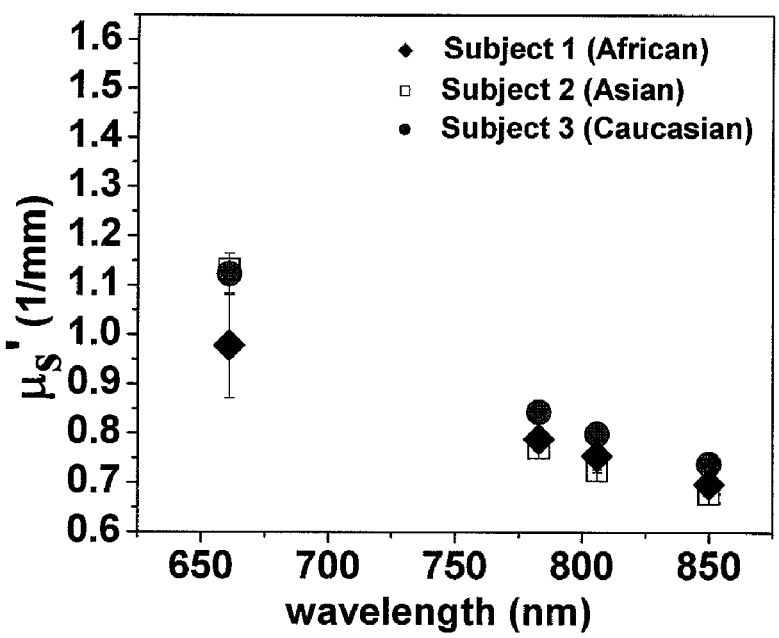

FIG. 13B illustrates the measured optical property ($\mu_s'$) as a function of wavelength for three subjects of different racial ethnicities (African, Asian, Caucasian).

Figure 14:
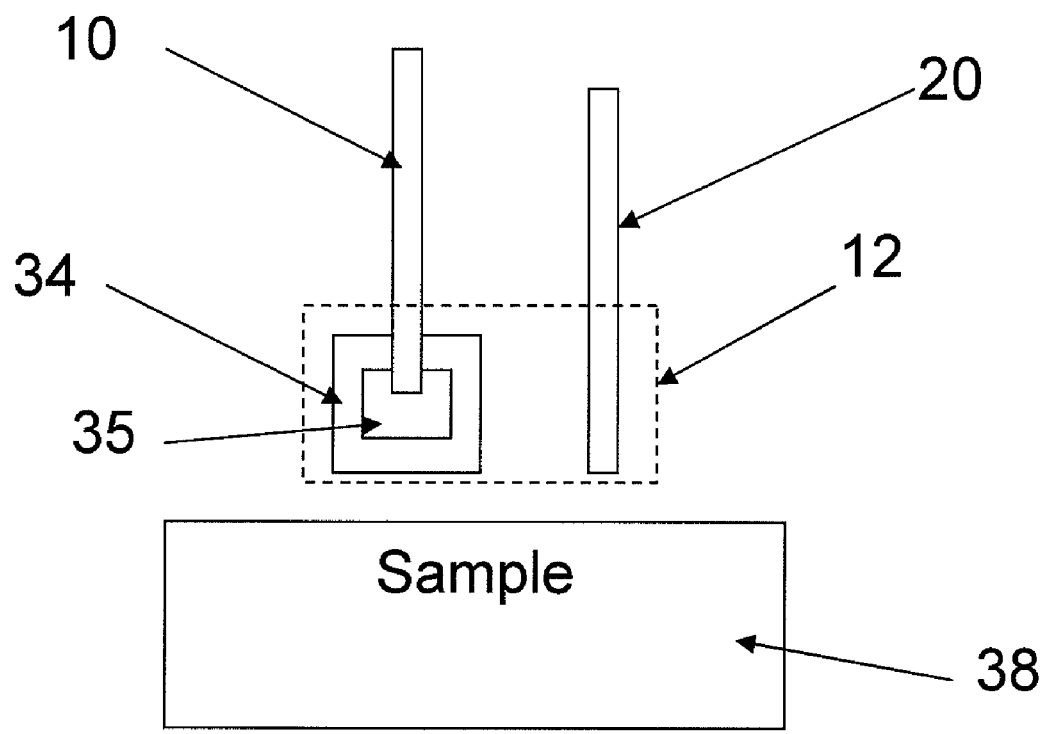

FIG. 14 illustrates a diffuse optical spectroscopy device according to another aspect of the invention.

DETAILED DESCRIPTION OF THE INVENTION

Figure 1:
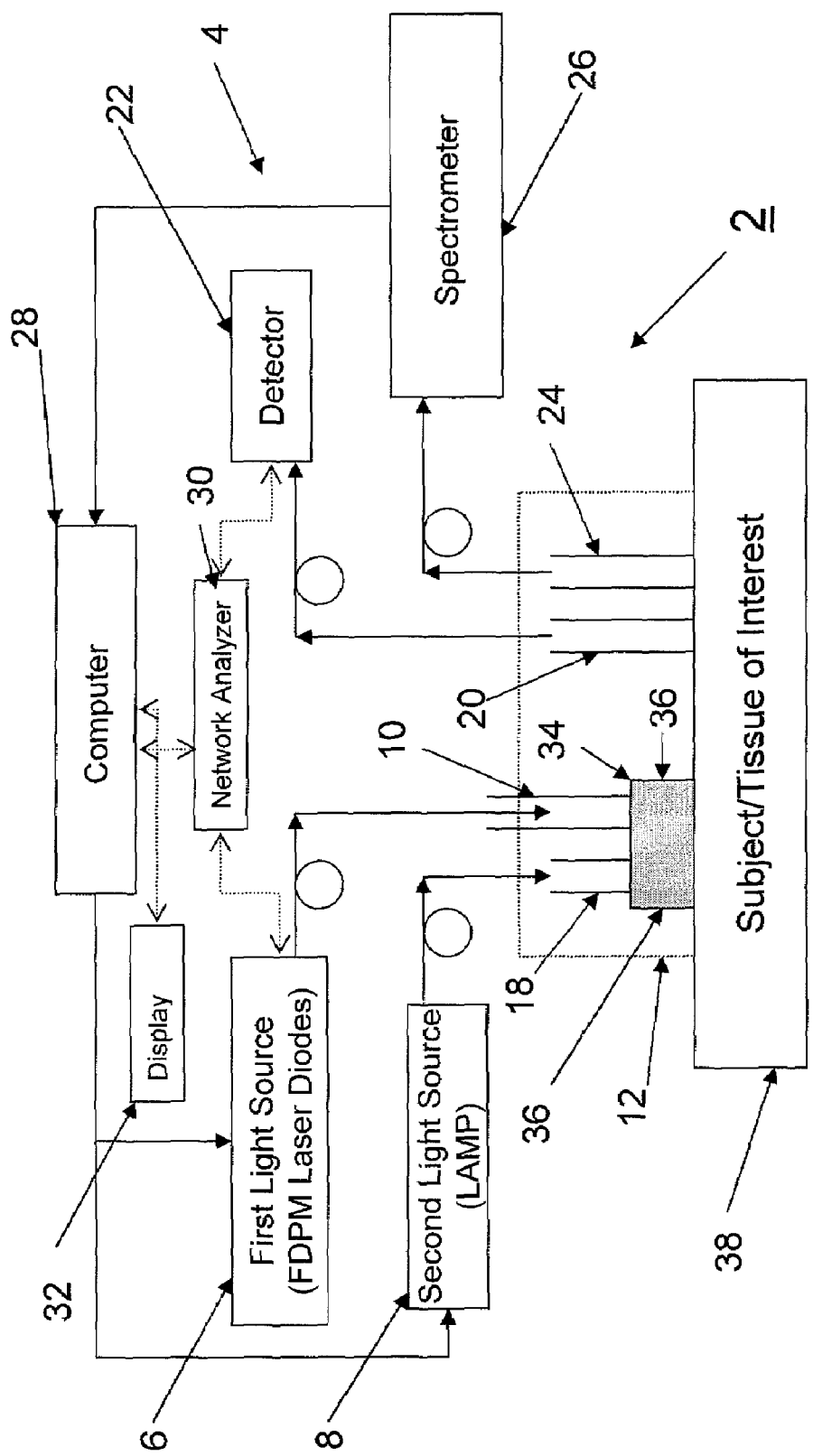
FIG. 1 illustrates a diffuse optical spectroscopy device according to one aspect of the invention.

FIG. 1 illustrates a diffuse optical spectroscopy (DOS) system 2 in accordance with a one aspect of invention. The system 2 generally includes a diffuse optical spectroscopy (DOS) device 4. The DOS device 4 includes a first light source 6 which preferably emits radiation at multiple wavelengths. For example, the first light source 6 may comprise multiple laser diodes each operating a different wavelengths. One exemplary example uses six laser diodes operating at wavelengths of 661 nm, 681 nm, 783 nm, 806 nm, 823 nm, and 850 nm. The plurality of laser diodes may be successively switched using a computer-controlled diode controller coupled to a series of RF switches (not shown). The first light source 6 may be other light sources capable of modulation. For example, LEDs could be used in place of laser diodes.

The first light source 6 preferably emits light having a wavelength with the range of 650 and 2500 nm. For applications that focus in the near-infrared (NIR) region, the first light source 6 emits light preferably in range of 650 nm to 1000 nm. This range of wavelengths is particularly useful for spectroscopic characterization of dysplastic oral tissue and skin cancer. For the quantitative and qualitative detection of chromophores in tissue, the first light source 6 preferably operates in the range of 900 nm to 2500 nm. In this wavelength region, the device 4 is sensitive to glucose, urea, lactose and a number of other analytes that may reflect a particular physiologic status or diseased state. In this spectral region, light transport is strongly modulated by water absorption, and consequently, probing depths may be no greater than a few hundred microns.

It should be noted that the system 2 is also amenable to quantitative spectroscopy at wavelengths shorter than the 650 nm to 1000 nm region. Light propagation at shorter wavelengths is, however, limited by high absorption and high scattering, which limits the utility of standard diffusion based models. However, by selection of an appropriate diffusing medium (as described in detail below), for example, SPECTRALON, available from Labsphere Inc., the system 2 could be applied using visible wavelengths, which because of larger absorption cross-sections with decreasing wavelength, may enable enhanced sensitivity to physiologic changes related to hemoglobin. It should be understood, however, that the system 2 and method is not limited to any particular range and may operate at wavelengths both above and below the above-identified ranges.

Figure 2A:
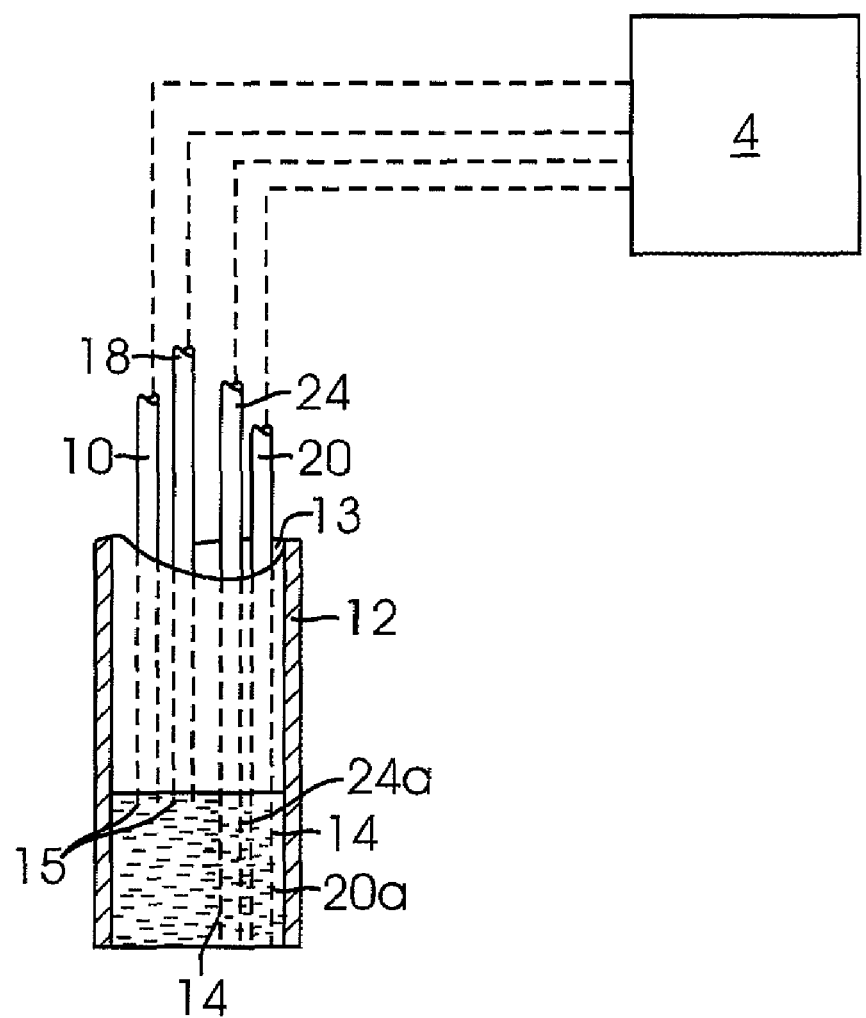
FIG. 2A illustrates a distal probe used with the DOS device of FIG. 1 according to one embodiment.
Figure 2B:
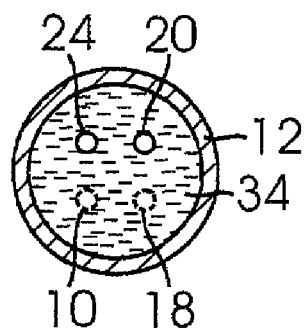
FIG. 2B illustrates an end view of the distal probe shown in FIG. 2A.

In one preferred embodiment, the DOS device 4 further includes a second light source 8 which generally serves as a broadband light source. The second light source 8 may comprise, for example, a tungsten-halogen light source (e.g., Ocean Optics S2000). A first source optical fiber 10 is provided that is connected at a proximal end to the first light source 6 (FIG. 1 shows the distal-most portion of the optical fiber 10). The opposing or distal end of the first source optical fiber 10 terminates in a probe 12 or other housing as is shown in FIGS. 1, 2A, 2B, 3, 4A, and 4B. As best seen in FIGS. 2A and 2B, the probe 12 may be formed from a plastic or other suitable material and includes a lumen 13 therein for receiving the optical fibers and a diffuser 34 (described in detail below). As best seen in FIG. 2A, the diffuser 34 is contained in the lumen 13 of the probe 12 at a distal end. The diffuser 34 is fixedly secured within the lumen 13 of the probe 12 using a press-fit arrangement or is secured through the use of an adhesive or mechanical attachment means (e.g., a screw, pin, or the like). The diffuser 34 is preferably located flush with the distal end of the probe 12 such that when the probe 12 is held against a sample or tissue of interest 38, the sample abuts the distal-most edge of the diffuser 34. As seen in FIG. 2A, the diffuser 34 includes therein a plurality of holes or bores 14 to receive optical fibers such as the detector optical fibers (20, 24). The holes or bores 14 for the detector optical fibers 20, 24 preferably pass through the entirety of the diffuser 34 such that distal ends of the detector optical fibers 20, 24 are flush with the distal-most edge of the diffuser 34.

Referring back to FIG. 1, the first detector optical fiber 20 is coupled at a proximal end to a detector 22 (FIG. 1 illustrates the distal portion of the first detector optical fiber 20). The detector 22 may include, for example, an avalanche photo diode (APD) detector (e.g., Hamamatsu high-speed APD module C5658-MOD-S6045-03). As explained above, the opposing or distal end of the first detector optical fiber 20 may terminate in a probe 12 or other housing. The opposing end of the first detector optical fiber 20 is then secured inside a hole or bore 14 in the probe 12 using an epoxy or other cementing material. Exemplary fibers that may be used as the first detector optical fiber 20 include, for example, a 600 μm multi-mode fiber.

The DOS device 4 includes a second detector optical fiber 24 that is coupled at a proximal end to a spectrometer 26. The spectrometer 26 preferably is able to acquire broadband reflectance measurements within the range of about 650 nm to about 1000 nm for applications that focus in the NIR region. The opposing or distal end of the second detector optical fiber 26, as explained above, may terminate in a probe 12 or other housing. The opposing end of the second detector optical fiber 24 is then secured inside a hole or bore 14 in the probe 12 using an epoxy or other cementing material. The second detector fiber 24 may be formed, for example, with a 600 µm multi-mode fiber.

The first and second detector optical fibers 20, 24 may be formed from smaller diameter fibers that those described above. For example, 100 µm (or even smaller) multi-mode or single mode fiber may be used to reduce the overall size of the probe 12.

Referring to FIGS. 2A and 2B, the circumferential surfaces 20a, 24a of the distal ends of the detector optical fibers 20, 24 are preferably coated or wrapped with an opaque substance (e.g., a coating or tape) to prevent light from scattering directly from the source optical fibers 10, 18 (described in detail below) to the detector optical fibers 20, 24.

With reference to FIGS. 2A and 2B, the distal ends of the first and second source optical fibers 10, 18 are optically connected to the diffuser 34. In one aspect of the invention, the distal-most ends of the first and second source optical fibers 10, 18 abut directly against a surface of the diffuser 34. In another aspect, as is shown in FIG. 2A, the distal-most ends of the first and second source optical fibers 10, 18 engage with shallow countersunk holes 15 formed in the diffuser 34. The first and second source optical fibers 10, 18 are preferably affixed to the diffuser 34 using an epoxy or other adhesive. Alternatively, the first and second source optical fibers 10, 18 may be inserted into the diffuser 34 in a friction or press-fit arrangement.

FIG. 2B illustrates an end view of the probe 12 according to one aspect of the invention. As seen in FIG. 2B, the first source optical fiber 10 is shown as a single fiber 10 disposed in a first quadrant of the probe 12 (lower left as shown in FIG. 2B). A second source optical fiber 18 is disposed in a second quadrant of the probe (lower right as shown in FIG. 2B). A first detector optical fiber 20 is located in a third quadrant of the probe 12 (upper right as shown in FIG. 2B). Generally, the first detector optical fiber 20 is diagonally opposed from the first source optical fiber 10. In one aspect of the invention, the first source optical fiber 10 is separated from the first detector optical fiber 20 by a distance of less than 5 mm. A second detector optical fiber 24 is located in a fourth quadrant of the probe 12 (upper left as shown in FIG. 2B). The second detector optical fiber 24 is generally located diagonally opposite from the second source optical fiber 18. In one aspect of the invention, the second source optical fiber 18 is separated from the second detector optical fiber 24 by a distance of less than 5 mm.

In a preferred aspect of the invention, the first source optical fiber 10 is a single fiber that is optically coupled to the respective laser diodes using one or more optical switches (not shown). Alternatively, the first source optical fiber 10 may consist of a bundle of separate fibers, with each fiber in the bundle being connected to a respective laser diode. The former embodiment is particularly advantageous in reducing the overall size of the probe 12.

Figure 3:
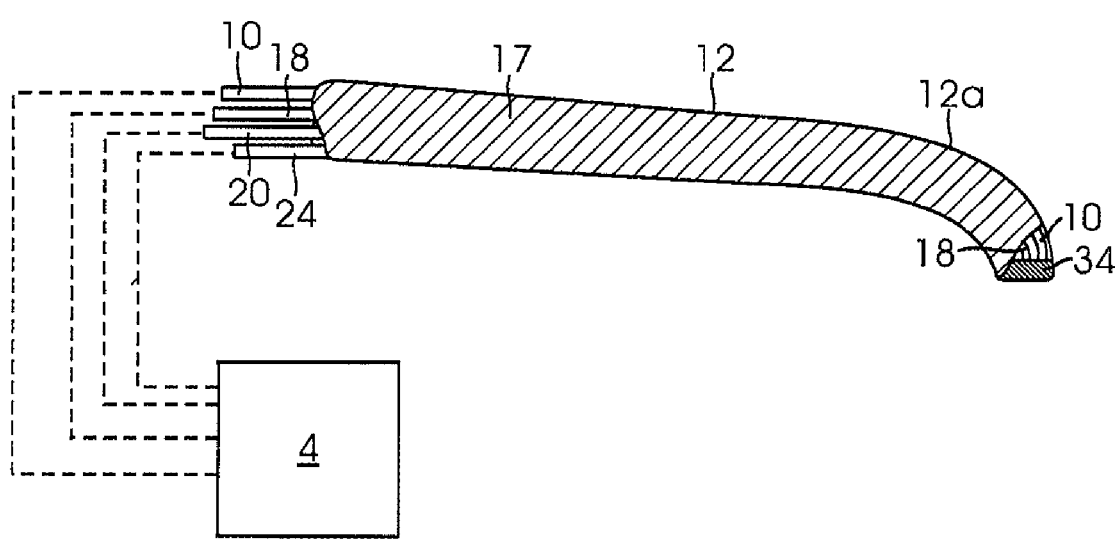
FIG. 3 illustrates a distal probe used with the DOS device of FIG. 1 according to another embodiment.

In one aspect of the invention, as best seen in FIG. 3, the probe 12 may include a bending portion 12a that bends the probe through approximately 90°. This particular arrangement of the probe 12 may be particular advantageous for use in the oral cavity of a subject 38. The probe shown in FIG. 3 includes a distal portion that is cut-away to permit viewing of the diffuser 34 and source optical fibers 10, 18. The probe 12 may be sized for easy manipulation by a user. For example, in the embodiment shown in FIG. 3, the probe 12 may have a length of about 10 cm. Still referring to FIG. 3, the probe 12 is preferably coated or wrapped in a sheath 17 (e.g., a disposable flexible sheath or wrap) that permits the probe 12 to be reused after sterilization.

With reference back to FIG. 1, the device 4 may include a computer 28 or central processor that is in electrical communication or otherwise interfaces with the first light source 6, the second light source 8, the detector 22, and spectrometer 26. The computer 28 may be a personal computer or the like having one or more data acquisition cards (not shown) for acquiring data from the detector 22 and spectrometer 26. Such data acquisition cards and the software for analyzing or manipulating the data are well known to those skilled in the art. In one aspect, the computer 28 may interface with or even include a network analyzer 30 that modulates the intensity and frequency of the first light source 6 (e.g., laser diodes).

The computer 28 and/or network analyzer 30 is preferably used to control the first light source 6 and the second light source 8. In addition, the computer 28 can be used to acquire data, calculate absorption and reduced scattering coefficients ($\mu_a$, $\mu_s'$), establish absolute reflectance intensities, and calculate concentrations. Of course, the computer 28 may also include a display 32 or the like to display useful information to a user. Moreover, the computer 28 may also be used to further manipulate the acquired data for subsequent analysis and/or display.

Referring to FIG. 1, a first source optical fiber 10 is optically coupled to the first light source 6 at a proximal end. The opposing end of the first optical source fiber 10 is used to deliver light to a sample or subject 38. The sample or subject 38 may comprise biological or even non-biological material. As best seen in FIG. 1, a diffuser 34 is interposed between the first source optical fiber 10, the second source optical fiber 18 and the sample 38. The diffuser 34 preferably comprises a material having a high scattering (high $\mu_s'$), low absorption (low $\mu_a$) material. The material forming the diffuser 34 effectively increases the photon path length from the distal end of the first source optical fiber 10 to the sample 38. The diffuser material may comprise a liquid, solid, or even semi-solid material. Examples of appropriate diffuser material include an intralipid such as, for example, LIPOSYN. Additional examples include plastics such as, for example, SPECTRALON, polytetrafluoroethylene (TEFLON), white DELRIN, and white optical-grade plastic material such as, for example, OP.DI.MA available from Gighertz-Optik, Inc., 5 Perry Way, Newburyport Mass. 01950-4009.

The diffuser material may also be formed from one or more powders which may be preferably embedded into a matrix such as, for example, silicone, epoxy, glass, or other similar matrix. Alternatively, the powder may simply be tightly packed into an enclosure or other housing (e.g., probe 12). Typical powders which scatter light efficiently and exhibit minimal absorption include barium sulfate, titanium dioxide, silicon dioxide (silica, etc.), polystyrene spheres (which can be obtained as a dry powder or in solution), latex spheres, and sugars such as Dextran. It should be understood that the above-noted materials are exemplary and other high scattering (high $\mu_s'$), low absorption (low $\mu_a$) materials may also be used in accordance with the invention. In one aspect of the invention, the diffuser 34 is made of a material having a $\mu_s'$ greater than 9 mm$^{-1}$ and a $\mu_a$ of about 0.0015 mm$^{-1}$ at 661 nm.

In one embodiment, as explained above, the diffuser 34 is located at the distal end of the first source optical fiber 10. For example, the diffuser 34 may physically abut against a distal end of the source optical fiber 10 or bundle of source optical fibers 10 (as well as the second source optical fiber 18). Alternatively, the diffuser 34 may be incorporated into or integrated with the first source optical fiber 10. The length or thickness of the diffuser 34 depends on the scattering ability of the material. Generally, a smaller thickness (e.g., path length) is required for materials having higher scattering values.

The $\mu_s'$ and $\mu_a$ values of the diffuser 34 are not limited to certain range. Rather, the values of $\mu_s'$ and $\mu_a$ that can be used in designing the diffuser 34 (e.g., a diffusive layer) are mainly determined by the $\mu_s'$ to $\mu_a$ ratio that satisfy the diffusion approximation. Generally, the ratio $\mu_s'/\mu_a$ should be at least larger than 10 in order to make diffusion approximation valid. The thickness of the layer is strongly dependent on the chosen $\mu_s'$ value. In order to satisfy the diffusion approximation, the diffuser thickness should be at least larger than $10*(1/\mu_s')$. The following are two examples of extreme, but valid cases. For a first limiting case (case 1), we can choose $\mu_s'$ to be 0.01/mm, and $\mu_a$ to be 0.001/mm. The top layer thickness given by $10*(1/\mu_s')$ is thus 1000 mm=1 m. For the second limiting case (case 2), we can choose $\mu_s'$ to be 1000/mm, and $\mu_a$=100/mm, and a top layer thickness=0.01 mm. Limiting case 1 is not practical for most clinical measurement because of the large top layer thickness. Limiting case 2 will require a high power light source 6 to acquire reasonable signal at detector 22 because the large $\mu_a$ of the top layer will introduce high attenuation (photons are absorbed) and the large $\mu_s'$ of the top layer will induce high diffuse reflectance (photons are reflected back to the medium above the top layer). Most applications will employ a combination of layer thickness, $\mu_s'$ and $\mu_a$ between these extremes.

For a diffuser 34 made of SPECTRALON, the thickness may fall within the range of about 0.5 mm to 2.0 mm. Preferably, the width (or diameter) of the diffuser 34 is the same as or similar to the diameter of the fist source optical fiber 10. This decreases the overall size of the device 4. In addition, in one embodiment, a reflective material 36 may be disposed on the lateral sides of the diffuser 34 (as shown, for example, in FIG. 1). Alternatively, the diffuser 34 may be incorporated into or held within the probe 12 distally from the first source optical fiber 10 as is shown in FIG. 3.

As explained above, the system 2 also includes a first detector optical fiber 20 that is used collect light and pass the same to a detector 22. The first detector optical fiber 20 may be disposed adjacent to or laterally disposed from the first source optical fiber 10. In FIG. 2B, the fist detector optical fiber 20 is laterally disposed diagonally from the first source optical fiber 10. The present system 2 and method allows for close spacing between the first source optical fiber 10 and the first detector optical fiber 20 while still maintaining the validity of diffusion approximation. In a preferred embodiment, the distal end of the first detector optical fiber 20 is separated from the distal end of the first source optical fiber 10 by less than 5 mm. The distance may even be reduced further to less than 5 mm between the distal ends of the fibers 10, 20. The diffusion approximation remains valid even at separation distances of 2.5 mm or less when the diffuser 34 is used.

In accordance with one aspect of the invention, the subject or tissue of interest 38 is irradiated with light from the first light source 6. The intensity-modulated diffuse reflectance signals are then detected using the detector 22. Next, the absorption and reduced scattering coefficients are determined at each wavelength of the first light source using the computer 28. This is accomplished by fitting phase and amplitude data to the analytical diffusion solution as explained, for example, in F. Bevilacqua et al., "Broadband absorption spectroscopy in turbid media by combined frequency-domain and steady-state methods," Appl. Opt. 39, 6498-6507 (2000), which is incorporated by references as if set forth fully herein.

Next, the subject or tissue of interest 38 is then irradiated with radiation from the second light source. Broadband reflectance measurements are then acquired using the spectrometer 26. The absolute reflectance spectra is then determined using the computer 28 based on the broadband reflectance measurements and the absorption and reduced scattering coefficients. Broadband absorption spectra ($\mu_a$) is then determined from the absolute reflectance spectra. The concentration of the tissue components are determined based on wavelength-dependent extinction coefficient spectra of each component. Typically, this last step is performed by using a least-squares fit of the absorption spectra of the components to the measured absorption spectrum over a range of wavelengths (e.g., 650 nm to 1000 nm).

While FIG. 1 illustrates a system 2 that includes both a FDPM and broadband aspect, it should be noted that the present system 2 and methods are applicable to a system 2 that includes only the FDPM aspect (i.e., first light source 6, first source optical fiber 10, first detector optical fiber 20, and detector 22) or a system 2 that only includes the broadband aspect (i.e., the second light source 8, second source optical fiber 18, second detector optical fiber 24, and the spectrometer 26).

Figure 4A:
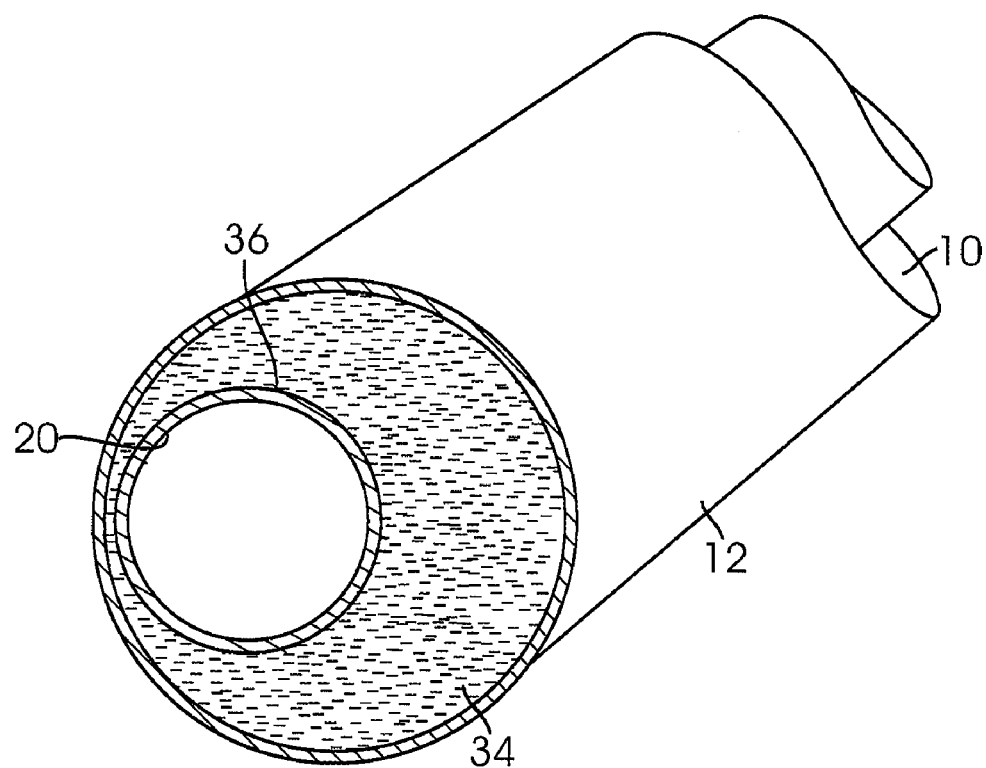
FIG. 4A illustrates an end view of the distal end of the diffuse optical spectroscopy device according to one embodiment.
Figure 4B:
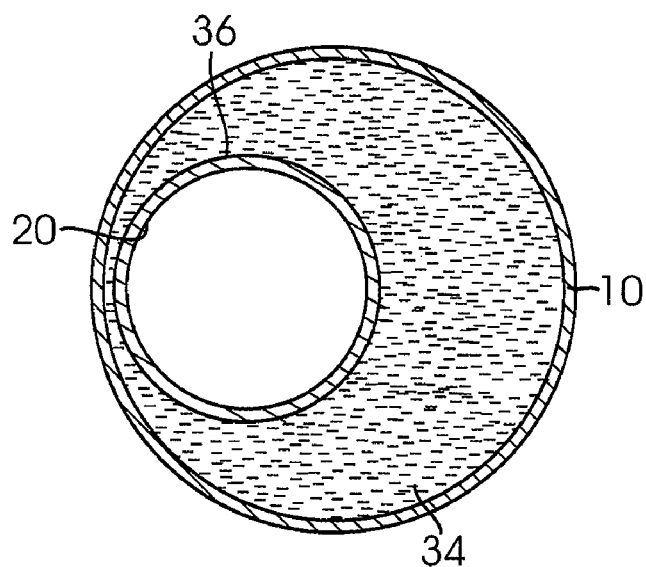
FIG. 4B illustrates an end view of the distal end of the diffuse optical spectroscopy shown in FIG. 4A.

FIG. 4A shows a partially cut-away view of the distal end of the FDPM portion of the probe 12 according to one preferred embodiment of the invention. In FIG. 4A, the first detector optical fiber 20 is disposed internal to the first source optical fiber 10. The first detector optical fiber 20 may be located coaxially within the first source optical fiber 10 or non-coaxially (as is shown in FIG. 4A). In the embodiment shown in FIG. 4A, a diffuser 34 fills a portion of the void between the exterior of the first detector optical fiber 20 and the interior of the first source optical fiber 10. In addition, an optional reflective surface 36 may be disposed between the diffuser 34 and the first detector optical fiber 20. FIG. 4B shows an end view of the distal end of the system 2 illustrated in FIG. 4A. As seen in FIG. 4B, the first detector optical fiber 20 is offset from the center axis of the first source optical fiber 10. It should be noted that other configurations are also contemplated by the invention, for example, the first detector optical fiber 20 may be aligned on the center axis of the first source optical fiber 10 (e.g., in a coaxial arrangement).

In one aspect of the invention, a common source optical fiber (shown, for example, as fiber 10 in FIG. 4A) may be used for both the first and second light sources 6, 8. Appropriate switching circuitry may be used to selectively connect the fiber 10 to the first and second light source 6, 8. Similarly, a common detector optical fiber (shown as fiber 20 in FIG. 4B) may be used to delivery reflected light to the detector 22 and spectrometer 26. Alternatively, a separate detector optical fiber for the spectrometer 26 may be disposed inside a common source optical fiber.

Figure 5A:
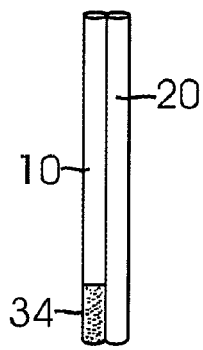
FIG. 5A illustrates the distal end of a diffuse optical spectroscopy device according to another aspect of the invention.
Figure 5B:
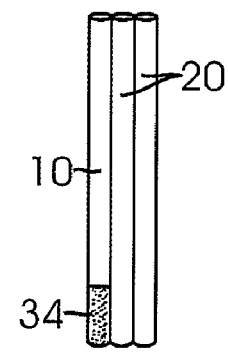
FIG. 5B illustrates the distal end of a diffuse optical spectroscopy device according to another aspect of the invention.
Figure 5C:
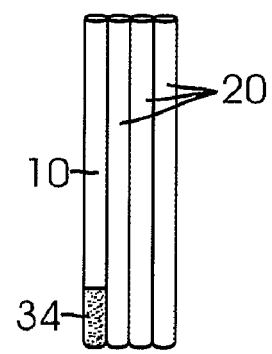
FIG. 5C illustrates the distal end of a diffuse optical spectroscopy device according to another aspect of the invention.

FIGS. 5A, 5B, and 5C illustrate the distal end of the system 2 according to an alternative embodiment. FIG. 5A illustrates an embodiment wherein the first source optical fiber 10 is located adjacent to the first detector optical fiber 20. In one alternative aspect, for example, if a bundle of multiple fibers is used for the first source optical fiber 10, the first single detector optical fiber 20 may located adjacent to the bundle of fibers. Alternatively, each source optical fiber 10 in the bundle may be associated with an adjacent detector optical fiber 20. In still another embodiment, if a single source optical fiber 10 is used, a single detector optical fiber 20 is located adjacent to the source optical fiber 10. This embodiment may be used, for example, within a probe 12 or other similar device in which it is particularly advantageous to reduce the overall size of the device. FIGS. 5B and 5C illustrate additional embodiments which use a plurality of detector optical fibers 20. Multiple detector optical fibers 20 may be associated with a single source optical fiber 10. Alternatively, multiple detector optical fibers 20 may be associated with multiple source optical fibers 10. Multiple detector optical fibers 20 generally increase the signal-to-noise ratio (SNR) of the system 2.

Figure 6:
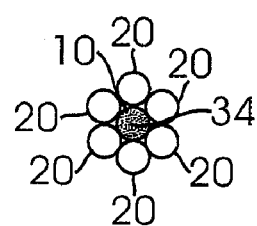
FIG. 6 illustrates an end view of the distal end of a diffuse optical spectroscopy device according to another aspect of the invention.

FIG. 6 illustrates an end view the distal end of a system 2 according to yet another embodiment. In FIG. 6, a central source optical fiber 10 is surrounded circumferentially by a plurality of detector optical fibers 20. The source optical fiber 10 may include a single source optical fiber 10 or, alternatively, the source optical fiber 10 may include a bundle of source optical fibers 10. The embodiment shown in FIG. 6 minimizes the overall size of the device because of the circumferential packing of the detector optical fibers 20 around the central source optical fiber 10 (or bundle of fibers) and may be particularly suited for incorporation into probes 12 and like where the available space to locate the fibers is small. Furthermore, as mentioned above, the additional detector optical fibers 20 tend to increase the SNR of the overall system 2.

Figure 7A:
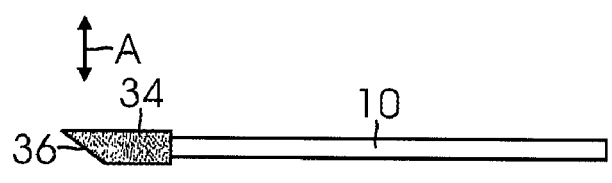
FIG. 7A illustrates a side view of the distal end of a diffuse optical spectroscopy device according to another aspect of the invention.
Figure 7B:
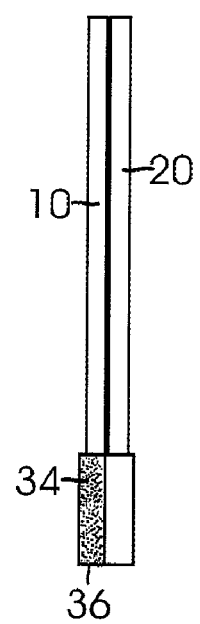
FIG. 7B illustrates a top view of the distal end of a diffuse optical spectroscopy device of FIG. 7A.

FIGS. 7A and 7B illustrate the distal end of a system 2 according to still another embodiment. In this embodiment, a side-firing arrangement is achieved in which light exits and enters the optical fibers 10, 20 generally perpendicular (see direction of arrow A in FIG. 7A) to the long axis of the fibers 10, 20. This can be accomplished, for example, by an angled diffuser 34 having a reflective surface 36 disposed on the angled surface to reflect the light generally perpendicular to the long axis of the fibers 10, 20. The detector optical fiber 20 may include a corresponding angled reflective surface 36 for receiving and transmitting light down the length of the fiber 20 (or multiple fibers 20). This side-firing arrangement is particularly useful when the probe 12 is affixed to the surface of the subject (e.g., a skin surface). In addition, this embodiment may be particularly suited for oral or intravascular applications.

The embodiment illustrated in FIGS. 7A and 7B may even be rotated to generate full 360° (or less) spectroscopic analysis of the interior surfaces of tissue. This may include, for example, the internal surface of a body cavity or even the vasculature of a patient. For example, the method and system 2 described herein may be useful in identifying vulnerable plaques and superficial lipid pools within the vasculature of a patient. Further, the system 2 and method may be used to quantitatively probe and monitor the superficial tissue layers in vascular tissue to monitor the inflammatory aspects that accompany the process of vulnerable plaque formation.

In one aspect of the invention, the diffuser 34 may be formed from a material that has variable absorption coefficient. For example, the diffuser 34 may have $\mu_a$ gradient formed across all or a portion of the diffuser 34. The diffuser 34 may be moveable or rotatable to expose the incoming light to different $\mu_a$ values. For example, if the diffuser 34 were formed in the shape of a disk, a gradient in $\mu_a$ might be established in the rotational direction $\phi$ such that rotation of the diffuser 34 about its central axis exposes the incoming light to varying $\mu_a$ values.

FIG. 14 illustrates one alternative probe 12 geometry that may be used with the DOS system 2. In this geometry, the diffuser 34 is formed with a cavity or hollow space 35 that is surrounded by diffusing material. The diffuser 34 may be formed in any number of shapes, for example, as a cube, sphere, or other shape. In one aspect of this embodiment, the hollow space 35 is filled with a material such as a liquid. For example, the walls or exterior of the diffuser 34 may be formed from a material having a first $\mu_s'$ value while different materials may be injected or otherwise disposed inside the hollow space 35 of the diffuser 34. For instance, liquids having different reduced scattering properties may disposed in the hollow space 35 of the diffuser 34 to control the interrogation depth of the sample 38.

FIG. 14 also illustrates the probe 12 (as well as the first source optical fiber 10 and the first detector optical fiber 20) being disposed some distance from the sample. It should be understood that the DOS systems 2 disclosed herein (e.g., those shown in FIGS. 1 and 14) may function without the probe 12 actually contacting the sample 38. Similarly, the source optical fiber 10 does not have to necessarily contact or abut the diffuser 34. A gap may be located between the distal end of the source optical fiber 10 and the diffuser 34. Likewise, the detector optical fiber 20 does not necessarily have to contact the sample 38 (as is shown in FIG. 14). For example, the source optical fiber 10 and the detector optical fiber 20 may be separated from the diffuser 34 and sample 38, respectively, by a fixed distance. Generally, having the source and detection fibers 10, 20 in close proximity to the diffuser 34 and sample, respectively, means better coupling of light from the source 6 to the sample 38 and back to the detector 22.

In still another aspect of the invention, the optical fibers 10, 20 may be omitted entirely from the DOS system 2. For example, the light source 6, such as LEDs or laser diodes might be embedded into or otherwise disposed directly in the diffuser 34. Similarly, on the detector arm of the system 2, a detector 22 such as a CCD and/or APD could be in direct contact with or disposed adjacent to the sample 38. In this embodiment, there would be no need for fibers 10, 20. The light source 6 and detector 22 may be incorporated directly into the probe 12.

The DOS system 2 can be used for determination of in-vivo optical properties of deep tissues, for quantifying tumor physiology, and for monitoring optical contrast agent dynamics. DOS has advantages of non-invasive interrogation of tissues, high contrast between normal and tumor tissue, and high spectral information.

In a preferred aspect of the invention, the DOS system 2 and method described herein can be employed to quantitatively characterize changes in epithelial tissues such as skin and oral mucosa that accompany dysplastic transformation. The probing depth needed to effectively target these superficial changes in tissue is generally less than 1 mm, which corresponds to a separation distance between the source optical fiber 10 and detector optical fiber 20 of less than 3 mm. In conventional DOS systems, with a separation distance of less than 5 mm, the diffusion approximation is no longer valid for most tissue types in the wavelength range from 650 nm-1000 nm.

An important distinction between the present system 2 and method and prior DOS devices is that the DOS system 2 and method described herein does not require the development of a representative, physiologically relevant "training set" of calibration samples and the related analyte concentrations. This prior multivariate approach has been commonly used in the non-invasive blood glucose monitoring industry, and it is difficult, time consuming, and costly to develop an empirical model based on multivariate approaches that will be stable for any individual for any reasonable period of time (weeks). However, until now, these approaches were the only recourse to quantitative spectroscopy because the spectral region of interest for many of these glucose oriented investigations (900 nm-2500 nm) is highly absorbing and low scattering and therefore inappropriate for the application of diffusion based modeling techniques.

The present system 2 and method also has applicability for quality control and process monitoring in the pharmaceutical industry. For example, tablet formulations are typically highly scattering, yet the dimensions of these are small and are not conducive to the usual photon migration based quantitative analyses. The disclosed method and system 2, however, may be useful for quantifying chemical constituents or species in tablet form.

The system 2 and method may also be used to perform quantitative fluorescence spectroscopy, which may be used to quantify metabolically important biochemicals. Alternatively, the method may be used to quantify exogenous fluorescent agents such as those used for photodynamic therapy and molecular imaging.

While the system 2 has been described herein as being used primarily for frequency domain diffuse optical spectroscopy, the diffuser 34 may also be used in other near infrared and optical spectroscopy methods, including, but not limited to, time domain and continuous wave spectroscopy.

EXPERIMENTAL RESULTS

Experiment 1

A DOS system 2 utilizing a diffuser 34 (in the form of a layer) was used to demonstrate that the validity of the diffusion approximation is maintained even as the source-detector separation distance is reduced to a distance of 2.5 mm. Frequency domain measurements were made at several wavelengths to recover the optical properties of tissue phantoms, using a two-layer model for which the optical properties and thickness of the upper, highly scattering layer were known.

In this approach, a high scattering, low absorption diffuser 34 layer was interposed between the distal end of the source optical fiber 10 and the sample source layer 38 ($\mu_s'=9$ mm$^{-1}$ and $\mu_a=0.0015$ mm$^{-1}$ at 661 nm). The diffuser 34 layer effectively increased the photon path length and allowed the source-detector separation to be made arbitrarily small. The general operation of the multi-wavelength frequency-domain spectroscopy system 2 is described in F. Bevilacqua, A. J. Berger, A. E. Cerussi, D. Jakubowski, and B. J. Tromberg, "Broadband absorption spectroscopy in turbid media by combined frequency-domain and steady-state methods," Appl. Opt. 39, 6498-6507 (2000) which is incorporated by reference as if set forth fully herein.

In the current experiment, laser diodes operating at wavelengths of 661 nm, 681 nm, 783 nm, 806 nm, 823 nm, and 850 nm were used to irradiate the tissue phantom layers 38. The modulation frequency for each diode was swept over a range between 50 MHz to 500 MHz. Photons were detected using a fiber-coupled avalanche photo-diode (e.g., Hamamatsu C5658-MOD-S6045-03 avalanche photo diode detector). The recorded amplitude demodulation and phase change were then fit to a light transport model based on diffusion approximation using a Levenberg-Marquardt minimization algorithm to determine the optical properties of the turbid samples 38.

Figure 8A:
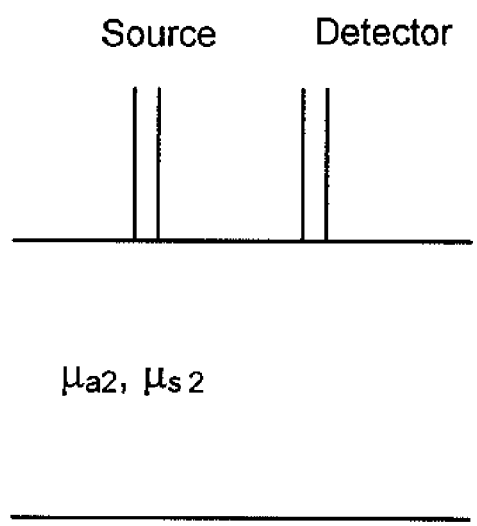
FIG. 8A illustrates the tissue phantom with optical properties $\mu_{a2}$, $\mu_{s2}'$ is the sample under investigation. The semi-infinite measurement geometry is illustrated.
Figure 8B:
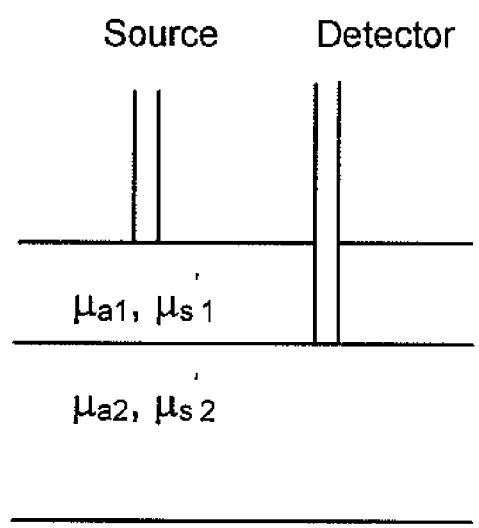
FIG. 8B illustrates the tissue phantom with optical properties $\mu_{a2}$, $\mu_{s2}'$ is the sample under investigation. The top layer with optical properties $\mu_{a1}$, $\mu_{s1}'$ is a high scattering, low absorption medium, in this case, undiluted 10% LIPOSYN.

A semi-infinite geometry as depicted in FIG. 8A is typically assumed for measurements of thick tissue. To increase the signal-to-noise ratio (SNR) and sensitivity to the bottom layer 38, a modified two-layer geometry (MTL) was used as is depicted in FIG. 8B. In this configuration, the detection fiber 20 was adjacent to and in contact with the sample of interest 38.

Three sets of measurements were conducted including: (1) 10 mm source-detector separation frequency domain measurements performed in semi-infinite geometry (i.e., no diffuser 34 present (e.g., no high scattering top layer)), (2) 5 mm source-detector separation frequency domain measurements performed in semi-infinite geometry (no high scattering top layer), and (3) 2.5 mm source-detector separation frequency domain measurement performed in the modified two-layer geometry having the diffuser 34 disposed between the distal end of the source optical fiber 10 and the sample of interest 38. The diffuser 34 or top layer had a thickness of 5 mm.

The semi-infinite measurements at 5 mm and 10 mm source-detector separations were made using a geometry as depicted in FIG. 8A. In addition, measurements were made at a 2.5 mm source-detector separation using a two-layer liquid phantom and geometry as shown in FIG. 8B. The high scattering, low absorption top layer (e.g., diffuser 34) used was undiluted 10% LIPOSYN, and the bottom layer tissue phantom 38 was constructed from a near-infrared absorbing dye (NIGROSIN), 10% LIPOSYN, and water. Transparent plastic wrap was used to separate upper and lower layers. All measurements were performed on the same liquid tissue phantom.

FIGS. 9A and 9B illustrate the recovered optical properties for the 10 mm semi-infinite geometry, the 2.5 mm MTL geometry, and the 5 mm semi-infinite geometry at six wavelengths. The square data points reflect the measurements made using the 10 mm semi-infinite geometry. The solid triangles represent the measurements of the 2.5 mm MTL geometry. Asterisks represent the measurements of the 5 mm semi-infinite geometry. The dashed line in FIG. 9A represents a power law fit to the reduced scattering coefficient measured at 10 mm source-detector separation in the semi-infinite geometry. FIG. 9A illustrates the agreement between the deduced $\mu_s'$ for the 10 mm semi-infinite geometry measurement and the 2.5 mm MTL geometry which follows the scattering power law fit. However, as seen in FIG. 9A, the $\mu_s'$ recovered using the 5 mm semi-infinite geometry measurement does not follow the scattering power law and the scatter in the data demonstrates the limitations of simple application of diffusion approximation when the source-detector separation is less than 5 scattering lengths (which for tissue in the wavelength range of 600 nm to 1000 nm is a few millimeters).

FIG. 9B shows the recovered $\mu_a$ at six wavelengths for the three measurement sets. The recovered $\mu_a$ in the 10 mm semi-infinite geometry measurement and the recovered $\mu_a$ from the 2.5 mm modified two-layer geometry show good agreement, while the recovered $\mu_a$ from measurements performed in the 5 mm semi-infinite geometry measurement are off by more than 50%. As seen in FIG. 9B, the values obtained for the absorption coefficient using the MTL geometry are in good agreement with the values obtained using the benchmark infinite multi-distance geometry.

FIGS. 10A and 10B illustrate the results of the recovered measurements of $\mu_s'$ and $\mu_a$, respectively at six wavelengths for a sample 38 having a low absorption and moderate scattering liquid phantom having optical properties similar to gingival (gum) tissue ($\mu_a \approx 0.012$/mm and $\mu_s' \approx 1.1$/mm at 660 nm). Measurements were carried out in modified two-layer (MTL) geometry (source-detector separation distance of 2.5 mm), semi-infinite (SI) geometry (source-detector separation distances of 2.8 mm, 5 mm, and 10 mm), and infinite geometry.

MTL and SI results were calibrated using a liquid phantom having $\mu_a \approx 0.02$/mm and $\mu_s' \approx 1.1$/mm at 660 nm. The dashed line in FIG. 10A is a power law fit to the reduced scattering coefficient measured at 2.5 mm source-detector separation in a MTL geometry. The solid line in FIG. 10A is a power law fit to the reduced scattering coefficient measured in a sample having the infinite geometry. FIG. 10B illustrates the measured values for the absorption coefficients. As seen in FIG. 10B, the measured absorption coefficient values using the MTL geometry agree with the benchmark infinite multi-distance geometry.

FIGS. 11A and 11B illustrate the results of the recovered measurements of $\mu_s'$ and $\mu_a$, respectively at six wavelengths for a sample 38 having a low absorption and low scattering liquid phantom having optical properties similar to cheek tissue ($\mu_a \approx 0.037$/mm and $\mu_s' \approx 0.67$/mm at 660 nm). The dashed line in FIG. 11A is a power law fit to the reduced scattering coefficient measured at 2.5 mm source-detector separation in a MTL geometry. The solid line in FIG. 11A is a power law fit to the reduced scattering coefficient measured in a sample having the infinite geometry. FIG. 11B illustrates the measured values for the absorption coefficients. As seen in FIG. 11B, the measured absorption coefficient values obtained using the MTL geometry are close to the results obtained with the benchmark infinite multi-distance geometry.

The results illustrate that optical properties recovered using a modified two-layer geometry with 2.5 mm source-detector separation are in good agreement with those obtained using a conventional 10 mm source-detector separation in the semi-infinite geometry. Monte-Carlo simulation may be used to fully characterize the limitations of the model and the probing depth of the modified two-layer geometry. Nonetheless, the present system 2 and method will enable the use of diffusion-based modeling techniques for source-detector separations in which diffusion based descriptions of light propagation are typically not valid.

Experiment 2

In a conventional DOS measurement in which the source optical fiber 10 and the detector optical fiber 20 are flush with sample 38 under investigation, a standard diffusion model is generally employed to recover sample's optical properties for its simplicity and efficiency. Unfortunately, the standard diffusion model is feasible only when the sample under investigation has $\mu_s'/\mu_a > 10$ and the source optical fiber 10 and detector optical fiber 20 separation distance is much larger than $1/(\mu_s' + \mu_a)$. In some applications, for example, measuring skin melanin concentration using NIR light, samples 38 have $\mu_s'$ on the same order of $\mu_a$, and the standard diffusion equation typically used is not appropriate for recovering optical properties of such samples 38.

The modified two-layer (MTL) geometry described herein uses a diffuser 34 in the form of a very high scattering top layer to make light radiance isotropic in a very short distance (1-2 mm). By using the diffuser 34, a diffusion model in MTL geometry is applicable for a MTL-based DOS device 4 with the assumption that the samples 38 have $\mu_s'/\mu_a > 1$. Moreover, a system 2 using the MTL geometry is capable of recovering the optical properties of samples having albedo values (i.e., $\mu_s'/\mu_a$) around 1 with small errors. In this particular experiment, measurements were performed on low albedo liquid phantoms. The diffuser 34 was formed of SPECTRALON. In particular, four liquid phantoms were fabricated (LP6, LP8, LP10, LP14) and their respective optical properties ($\mu_s'$, $\mu_a$) were measured at a wavelength of 783 nm. The measured optical properties of each liquid phantom and their respective albedo values are listed below in Table 1.

TABLE 1

|  | LP6 | LP8 | LP10 | LP14 |
| --- | --- | --- | --- | --- |
| $\mu_a$ (mm$^{-1}$) | 0.041 | 0.158 | 0.623 | 0.771 |
| $\mu_s'$ (mm$^{-1}$) | 0.819 | 0.819 | 0.819 | 0.5 |
| $\mu_s'/\mu_a$ | 19.98 | 5.18 | 1.31 | 0.65 |

As seen in Table 1, albedo values of the liquid phantoms range from about 20 to 0.65. In addition, a DOS system 2 using the MTL geometry recovered the optical properties of each liquid phantom. FIG. 12 illustrates the deviation of the derived optical properties from the true optical properties for each liquid phantom. It can be seen from FIG. 12 that the recovered optical properties for the LP14 sample (albedo=0.65) have percent deviations lower than approximately 22%. It should be noted that because the top layer (i.e., diffuser 34) is a very high scattering layer whose reflectance coefficient is very high. Thus, the transmission rate of photons from the light source penetrating the top layer to the sample is low (around 5%). Consequently, the signal-to-noise ratio (SNR) at the detector 22 is low. In addition, the SNR at the detector is further reduced if the MTL probe 12 is applied on a sample 38 having a low albedo value. The percentage error of the recovered optical properties for low albedo samples 38 can be mitigated or reduced by improving instrumentation such as using higher power output laser diodes 10 and higher SNR detectors 22. For example, the use of multiple detector fibers 20 may increase the overall SNR of the device 4.

Experiment 3

The optical properties ($\mu_s'$, $\mu_a$) of human skin were determined by using MTL-based DOS system 2. Measurements were made in vivo in a non-invasive manner. In this experiment, the optical properties of forearm skin of three healthy subjects were measured. The subjects were of African, Caucasian, and Asian descent. The optical properties ($\mu_s'$, $\mu_a$) were determined at four different wavelengths using the DOS system 2 described herein. FIGS. 13A and 13B illustrate the measured optical properties ($\mu_s'$, $\mu_a$) as a function of the different wavelengths for each subject. The measured $\mu_a$ of the forearm skin of the African subject is much higher than those of the other two subjects (around 500% higher at 660 nm). In contrast, the $\mu_s'$ of the skin of the three subjects were generally close to one another (generally within 10% for most of wavelengths). It is believed that the $\mu_a$ differences in this wavelength range are mainly due to the differences in melanin concentration of three subjects. Consequently, the DOS system 2 and methods described herein are able to quantitatively measure melanin concentration in vivo, in a non-invasive manner.

The measured in vivo skin absorption difference between the Caucasian and African subjects are consistent with the ex vivo absorption coefficients obtained by others. See eg., C R Simpson et al., Phys. Med. Biol. 43 (1998) 2465-2478. Moreover, the measured in vivo reduced scattering coefficients are consistent with Simpson et al.'s ex-vivo measurement results which show that African and Caucasian subjects have similar reduced scattering coefficients over the wavelength range from 600 nm to 1000 nm. The reduced scattering coefficients measured using the MTL-based DOS system 2 possess the same trend as the results obtained by Simpson et al.

The higher values of measured reduced scattering coefficients obtained by Simpson et al. could be introduced by the fact that measurements were made on ex vivo skin which likely has a lower fraction of water and blood than those of in vivo skin. A deficiency of water and/or blood in tissue may induce higher index mismatch at scatter-tissue boundaries, such as vessel-tissue boundaries and cell-tissue boundaries. Consequently, scattering in the tissue will become stronger in ex vivo samples of skin.

While embodiments of the present invention have been shown and described, various modifications may be made without departing from the scope of the present invention. The invention, therefore, should not be limited, except to the following claims, and their equivalents.

We claim:

1. A diffuse optical spectroscopy device for obtaining the optical properties of a sample comprising:
    a computer;
    a first light source operatively connected to the computer;
    a first source optical fiber coupled to the first light source at one end and configured to illuminate the sample with light from the first light source at another end;
    a detector operatively connected to the computer;
    a first detector optical fiber coupled to the detector at one end and configured to receive light from the sample;
    a second broadband light source operatively connected to the computer;
    a second source optical fiber coupled to the second light source at one end and configured to illuminate the sample with light from the second broadband light source at another end;
    a spectrometer operatively connected the computer;
    a second detector optical fiber coupled to the spectrometer at one end and configured to receive light from the sample; and
    a diffuser interposed between the first source optical fiber and the sample, the diffuser comprising a material having a reduced scattering coefficient greater than 9 $mm^{-1}$.

2. The device of claim 1, wherein the first light source is a coherent light source having a wavelength within the range of between about 650 nm and about 1000 nm.

3. The device of claim 1, wherein the first light source is a coherent light source having a wavelength within the range of between about 900 nm and about 2500 nm.

4. The device of claim 1, wherein the diffuser comprises a liquid.

5. The device of claim 1, wherein the diffuser comprises a solid.

6. The device of claim 1, wherein the diffuser comprises a gel.

7. The device of claim 1, wherein the first source optical fiber is separated from the first detector optical fiber by a distance less than 5 mm at a distal end.

8. The device of claim 1, wherein the first detector optical fiber is located adjacent to the first source optical fiber.

9. The device of claim 1, wherein the first detector optical fiber is contained within the first source optical fiber.

10. The device of claim 1, wherein at least one of the first and second detector optical fibers comprises a plurality of detector optical fibers, each of the plurality of detector optical fibers being separated from the first source optical fiber by a distance of less than 5 mm at a distal end.

11. The device of claim 1, further comprising a probe housing the first source optical fiber, the first detector optical fiber, the second source optical fiber, the second detector optical fiber, and the diffuser.

12. The device of claim 1, further comprising a reflective coating disposed on a surface of the diffuser.

13. A diffuse optical spectroscopy device for obtaining the optical properties of a sample comprising:
    a computer;
    a first light source operatively connected to the computer;
    a first source optical fiber having a proximal end and a distal end, the first source optical fiber being optically coupled to the first light source at the proximal end, the distal end being configured to illuminate the sample with light from the first light source;
    a first detector optical fiber having a proximal end and a distal end, the first detector optical fiber being optically coupled to a detector at the proximal end, the distal end being configured to receive light from the sample;
    a broadband light source operatively connected to the computer;
    a second source optical fiber having a proximal end and a distal end, the second source optical fiber being optically coupled to the broadband light source at the proximal end, the distal end being configured to illuminate the sample with light from the broadband light source;
    a spectrometer operatively connected to the computer;
    a second detector optical fiber having a proximal end and a distal end, the second detector optical fiber being optically coupled to the spectrometer at the proximal end, the distal end being configured to receive light from the sample;
    a diffuser interposed between the distal end of the first source optical fiber and the sample; and
    wherein the distal end of the first source optical fiber and the distal end of the first detector optical fiber are separated by a distance of less than 5 mm.

14. The device of claim 13, wherein the distal end of the first source optical fiber and the distal end of the first detector optical fiber are separated by a distance of less than 2.5 mm.

15. A method of performing diffuse optical spectroscopy (DOS) on a sample comprising the steps of:
    providing a DOS device having a first light source, a first source optical fiber having a proximal end and a distal end, the first source optical fiber being optically coupled to the first light source at the proximal end, a first detector optical fiber having a proximal end and a distal end, the first detector optical fiber being optically coupled to a detector at the proximal end, a broadband light source, a second source optical fiber having a proximal end and a distal end, the second source optical fiber being optically coupled to the broadband light source at the proximal end, a second detector optical fiber having a proximal end and a distal end, the second detector optical fiber being optically coupled to a spectrometer at the proximal end, and a diffuser interposed between the distal end of the first source optical fiber and the sample;

illuminating the sample with light from the first light source using the first source optical fiber, the light passing through the diffuser;

detecting reflected light from the sample with the detector coupled to the first detector optical fiber;

illuminating the sample with light from the second light source using the second source optical fiber; and detecting reflected light from the sample with the spectrometer coupled to the second detector optical fiber.

16. The method of claim 15, wherein the diffuser comprises a material having a reduced scattering coefficient greater than 9 mm$^{-1}$.

17. The method of claim 16, wherein the diffuser material has a reduced scattering coefficient ($\mu_s'$) and an absorption coefficient ($\mu_a$) such that the ratio of $\mu_s'/\mu_a$ is greater than or equal to 10.

18. The method of claim 15, wherein the distal end of the first source optical fiber and the distal end of the first detector optical fiber are separated by a distance of less than 5 mm.

19. The method of claim 15, further comprising the step of determining the reduced scattering coefficient ($\mu_s'$) and the absorption coefficient ($\mu_a$) of the sample and quantifying the concentration of a chromophore contained in the sample based at least in part on the reduced scattering coefficient ($\mu_s'$) and the absorption coefficient ($\mu_a$).

* * * * *